(12) United States Patent
Piccariello et al.

(10) Patent No.: US 7,438,900 B2
(45) Date of Patent: Oct. 21, 2008

(54) DENDRITIC ENCAPSULATION OF ACTIVE AGENTS

(75) Inventors: Thomas Piccariello, Blacksburg, VA (US); Travis Mickle, Charlottesville, VA (US); Barney Bishop, Annandale, VA (US)

(73) Assignee: Shire LLC, Florence, KY (US)

( * ) Notice: Subject to any disclaimer, the term of this patent is extended or adjusted under 35 U.S.C. 154(b) by 446 days.

(21) Appl. No.: 10/885,878

(22) Filed: Jul. 8, 2004

(65) Prior Publication Data

US 2005/0069550 A1    Mar. 31, 2005

(51) Int. Cl.
*A61K 31/335*    (2006.01)

(52) U.S. Cl. .................. 424/78.13; 514/449; 514/461; 514/468

(58) Field of Classification Search ........................ None
See application file for complete search history.

(56) References Cited

U.S. PATENT DOCUMENTS

| | | | |
|---|---|---|---|
| 5,463,022 A | 10/1995 | Inoue et al. | |
| 5,700,459 A | 12/1997 | Krone et al. | |
| 7,060,708 B2 * | 6/2006 | Piccariello et al. | .......... 514/282 |

FOREIGN PATENT DOCUMENTS

WO    WO 97/10829    3/1997

OTHER PUBLICATIONS

International Search Report dated Sep. 16, 2003, for PCT/US03/00379, filed Jan. 8, 2003.

* cited by examiner

*Primary Examiner*—Anish Gupta
(74) *Attorney, Agent, or Firm*—Darby & Darby (57) ABSTRACT

A pharmaceutical composition comprising an active agent bound to a scaffold for dendritic encapsulation wherein said scaffold is covalently or non-covalently attached to a polysaccharide. More specifically, the invention is directed to active agent complexes or conjugates which utilize dendritic encapsulation alone or in combination with other delivery systems to improve and target active agent release.

5 Claims, 5 Drawing Sheets

DENDRITIC ENCAPSULATION OF ACTIVE AGENTS

CROSS-RELATED APPLICATIONS

This application claims priority to PCT/US03/00379, filed Jan. 8, 2003, which claims the benefit of provisional application 60/345,650 filed Jan. 8, 2002, both of which are hereby incorporated by reference in their entirety.

FIELD OF THE INVENTION

The present invention relates to active agent delivery systems and methods for protecting and administering active agents. More specifically, the invention is directed to active agent complexes or conjugates which utilize dendritic encapsulation alone or in combination with other delivery systems to improve and target active agent release.

In addition to their common meaning the following terms may further be defined as follows. Scaffold: a molecular entity whereby multiple agents can be attached to form a dendritic structure. Dendritic glycopeptide: a construct of multiple polysaccharides covalently attached to a central peptide. Dendrite: multiple polysaccharides branching from a central scaffold. Ligation: the formation of non-covalent bonds between two molecular entities; the energy of the bond being derived from lipophilic interactions, hydrogen bonding, Van der Waals forces or ionic bonding.

Therapeutic peptide: a pharmaceutically active molecule that is made of amino acids linked through amide bonds. Peptide-drug conjugate: a molecular construct comprised of a peptide and a small molecule covalently bonded. Peptide is meant to include small peptide chains, i.e. 2-10 amino acids, as well as larger oligopeptides and polypeptides.

Internal release mechanism: a mechanism where a masked nucleophilic moiety in close proximity to an active agent attached to a cleavage site on the same molecule, affects cleavage after the nucleophile is unmasked thereby releasing the active agent.

SUMMARY OF THE INVENTION

The invention provides for a pharmaceutical composition comprising an active agent bound to a peptide scaffold for dendritic encapsulation wherein said peptide scaffold is covalently attached to a polysaccharide. The peptide scaffold may serve as a ligand for non-covalent binding of an active agent. In one embodiment the active agent is a peptide-drug conjugate. In another embodiment the peptide scaffold serves as a ligand for covalent binding of an active agent. The active agent for instance may also be an azo compound or a nitro compound.

In another embodiment the active agent is non-covalently incorporated into the higher order structure of the polysaccharide dendrite. In one embodiment of the invention, the non-covalent incorporation is a result of ligand-receptor interaction, lipophilic interactions, Van der Waals forces, ionic bonding, hydrogen bonding.

In another embodiment the active agent is covalently incorporated into the polysaccharide dendrite. The covalent incorporation may be a result of an azide, amide, thioester, disulfide, ester, carbonate, carbamate or ureide bond. Further, the active agent may be attached to the scaffold via the side chains, the amino terminal residue, the carboxy terminal residue, or combinations thereof. In another embodiment, the non-attached portion of the amino acid, oligopeptide, polypeptide or polysaccharide is in its natural form (e.g. unprotected).

In another embodiment, an active agent is covalently attached to a peptide and the peptide active agent conjugate is further attached to a polysaccharide dendrite.

Various embodiments of the invention provide for delivery of the active agent through mediated release under specific body conditions. For instance, the invention may be formulated to release the pharmaceutically active compound in the colon, small intestine, or stomach depending on the formulation. The invention provides for the mediated delivery mechanisms, for instance, following oral, parenterally, injection or inhalation.

In another embodiment of the invention, the scaffold comprises a plant glycoside. The plant glycoside may be for instance, a glycosylated flavanol, diterpenoid, anthraquinone or like substance. In one embodiment, the plant glycoside serves as a scaffold for covalent attachment of a polysaccharide. In another embodiment, the plant glycoside serves as a scaffold for non-covalent attachment of a peptide active agent conjugate. In other embodiment, the plant glycoside serves as a scaffold for covalent attachment of a peptide active agent conjugate. In another embodiment, the plant glycoside serves as a scaffold for covalent attachment of a small molecule active agent.

Further, the invention provides for a pharmaceutical composition comprised of a peptide (or oligonucleotide) incorporating polysaccharide dendrites for delivery of a pharmaceutically active compound wherein the peptide (or oligonucleotide) serves as a scaffold for dendritic encapsulation by covalent attachment of polysaccharides. Alternatively, the peptide (or oligonucleotide) scaffold may serve as a ligand for non-covalent binding of a therapeutic peptide (or peptide-drug conjugate). Further, the peptide (or oligonucleotide) scaffold may serve as a point of covalent attachment for the therapeutic peptide (or peptide-drug conjugate).

The invention also provides for a pharmaceutical composition wherein a therapeutic peptide is bound to the peptide (or oligonucleotide) incorporating polysaccharide dendrites. The therapeutic peptide may be non-covalently (e.g. ligand-receptor interaction, lipophilic interactions, Van der Waals forces, ionic bonding, hydrogen bonding) attached to the scaffold peptide (or oligonucleotide). Alternatively, the therapeutic peptide is covalently attached to the peptide (or oligonucleotide) incorporating polysaccharide dendrites. Further, the therapeutic peptide may be covalently (e.g. azide, amide, thioester, disulfide, ester, carbonate, carbamate or ureide bonds) attached via the side chains and/or the amino terminal and/or carboxy terminal residues of the scaffold.

The invention also provides for a pharmaceutical composition wherein a peptide containing a pharmaceutically active compound covalently attached to it is attached to the peptide (or oligonucleotide) containing polysaccharide dendrites, (e.g. a peptide-drug conjugate delivered by dendritic encapsulation).

The invention also provides a pharmaceutical composition comprised of a plant glycoside aglycone (e.g., flavanol, diterpenoid or anthraquinone) which incorporates polysaccharide dendrites for delivery of a pharmaceutically active compound wherein the aglycone serves as a scaffold for dendritic encapsulation by covalent attachment of polysaccharides. Alternatively, the aglycone scaffold may serve as a ligand for non-covalent binding of a therapeutic peptide (or peptide-drug conjugate). The aglycone scaffold may serve as a point of covalent attachment for the therapeutic peptide (or peptide-drug conjugate). Further, the aglycone scaffold may serve as a point of covalent attachment for a small molecule therapeutic agent.

The invention also provides a pharmaceutical composition comprised of an azo compound or a nitro compound incorporating polysaccharide dendrites for delivery of a pharmaceutically active compound wherein the azo compound or a nitro compound serves as a scaffold for dendritic encapsulation by covalent attachment of polysaccharides. Alternatively, the azo compound or a nitro compound scaffold may serve as a ligand for non-covalent binding of a therapeutic peptide (or peptide-drug conjugate). The azo compound or a nitro compound scaffold may serve also as a point of covalent attachment for the therapeutic peptide (or peptide-drug conjugate). Further, the azo compound or a nitro compound scaffold may serve as a point of covalent attachment for a small molecule therapeutic agent. In another embodiment the azo compound or nitro compound are not scaffolds for dendritic encapsulation.

The invention provides the ability to design active agent complexes that result in specific delivery of the active agent. For instance active agents may be selectively delivered to the colon via protection of pharmaceutically active agent from enzymatic digestion by stomach and small intestinal enzymes. In another embodiment, the active agent may be protected from serum enzymes, liver metabolism, and elimination by kidneys. Additionally, another embodiment provides protection of pharmaceutically active agent from enzymes in the respiratory tract (e.g. elastase).

DETAILED DESCRIPTION

For almost all of the drugs in the Pharmacopoeia the majority of absorption, if not all of it, occurs in the small intestine. For some drugs, however, absorption may occur in the colon (e.g. analgesics); the relative extent of absorption has not been well studied, however. Sustaining the release of drugs would improve their clinical efficacy, especially for drugs requiring multiple dosing or where their therapeutic window is somewhat narrow. For those drugs that could benefit from sustained release pharmacokinetics and are absorbed in the colon, providing additional availability to the colon would be a significant improvement. This increased efficacy is more pronounced by the realization that the transit time in the colon can be as much as ten times that of the small intestine.

Some of the drugs that are used to treat ulcerative colitis include 5-aminosalicylates (e.g. mesalamine), corticosteroids (e.g. dexamethasone), metronidazole, 6-mercaptopurine, methotrexate and cyclosporine. Delivering these drugs to the colon specifically should improve their efficacy. Delivery of small peptides, such as cyclosporine, to the colon is especially challenging given the peptidase activity in the small intestines. Dexamethasone has been delivered to the colon by combining it with dextran. Furthermore, both metronidazole and celecoxib have been targeted for colonic delivery using guar gum as a carrier.

Delivery of drugs to certain regions or organs of the body can be accomplished by protecting the drug from decomposition and/or from attachment to binding sites prior to the drug reaching the target site. Micellar encapsulation, polymeric formulation and enteric coating are a few examples of methods used to "protect" a drug in vivo. There a very few examples, however, that exploit the enzymatic specificity in the colon to affect active agent release from the protective agent.

Perhaps the most appropriate protective agent for colonic delivery is a polysaccharide and for good reason. Polysaccharides are more resistant to hydrolysis in the stomach and small intestines than in the colon. This is because the majority of glycosidases that exist in the animal are actually secreted by bacteria and the colon has, by far, the greatest population of microflora in a healthy animal. It should be pointed out, however, that there are other classes of compounds known to pass through the small intestines into the colon, which include plant glycosides, azo compounds and nitro compounds.

Figure 1:
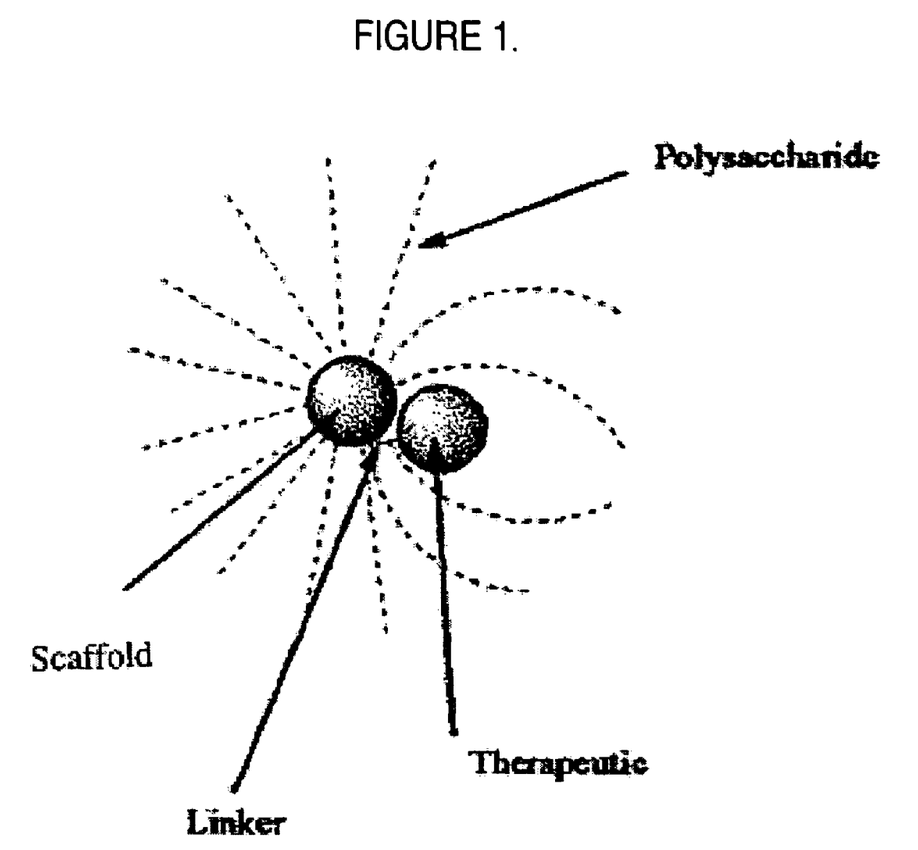
FIG. 1 provides a diagram of a proposed dendritic construct.

In dendritic encapsulation (FIG. 1), the therapeutic agent is bound to a core molecular entity, the scaffold. The scaffold can be any multifunctional molecule allowing for attachment of the therapeutic agent and at least one saccharide moiety. The scaffold is selected from a group consisting of amino acids, carbohydrates, purines or combinations thereof. The therapeutic agent can be linked to the scaffold by a covalent bond that is readily hydrolyzed under physiological conditions (i.e. azide, thioester, disulfide, ester, carbonate, carbamate or ureide). Alternatively, the scaffold and the therapeutic agent can be non-covalently bound to each other. In either case, the scaffold serves as a platform to which multiple polysaccharide chains can be affixed. By varying chain length and composition, the polysaccharides will provide a shell enclosing the scaffold and the therapeutic agent. This "shell" prevents absorption of the therapeutic agent and shields peptidic therapeutic agents from digestive enzymes in the stomach and intestines. Microflora in the colon break down the polysaccharide coating exposing the scaffold-therapeutic linkage, making it accessible for hydrolysis and release of the drug.

The digestive properties of the polysaccharides in different organs can be used to select the polysaccharide portion of the dendritic construct. For example, starch is digested in the small intestines and may not be the ideal polysaccharide for dendritic encapsulation. Non-starch polysaccharides, on the other hand, escape intestinal digestion and thus may be a viable candidate for dendritic encapsulation. Some low molecular weight dietary carbohydrates, such as stachyose and raffinose, are not digested in the small intestines. Even some disaccharides, such as lactulose, palatinose, maltitol and lactitol have been shown to reach the colon in large proportion relative to what was ingested.

Figure 2:
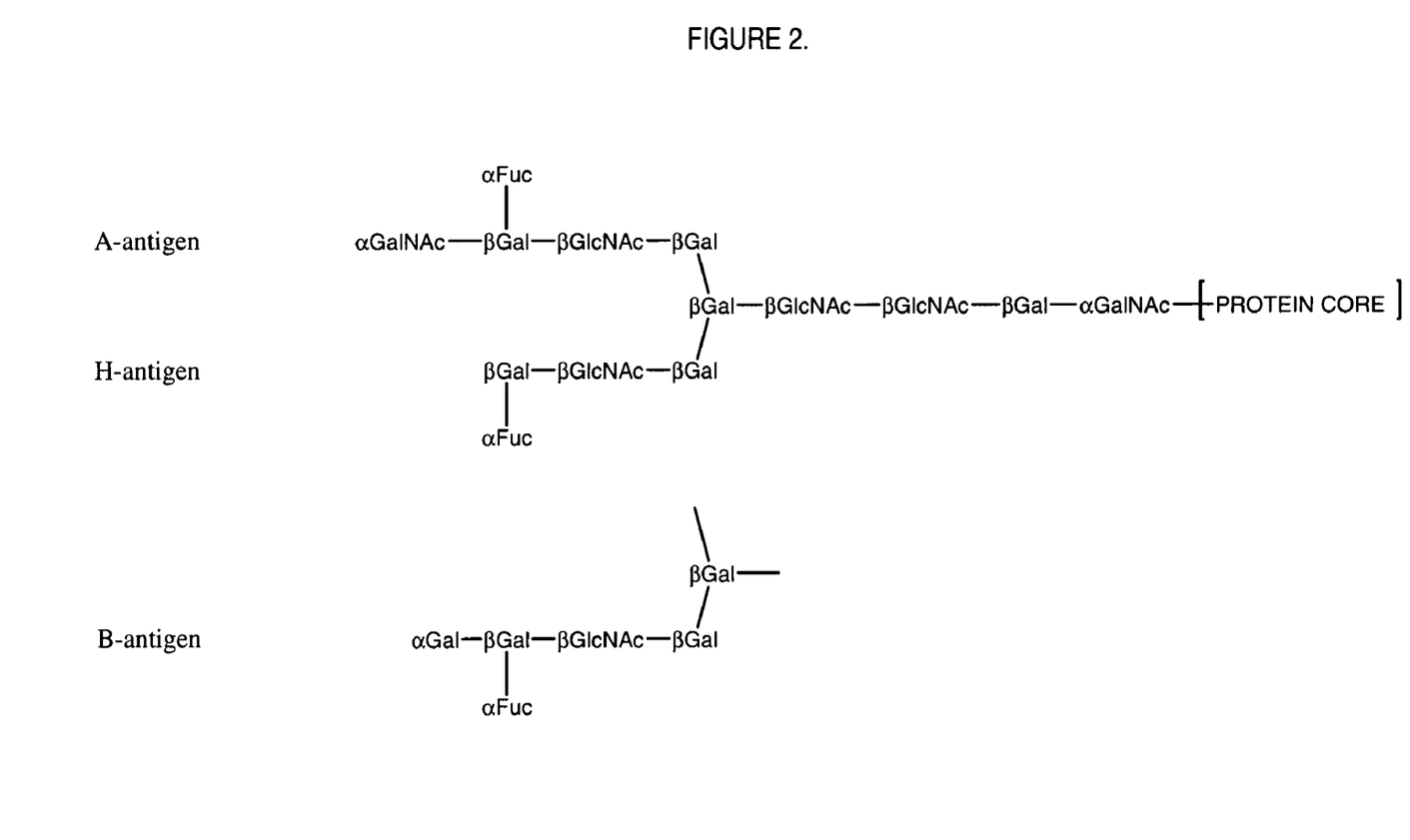
FIG. 2 depicts the structure of A, B and H blood group antigens of mucin.

Glycosidases secreted by colonic bacteria are capable of digesting a wide variety of carbohydrates. Most of the carbohydrate source is dietary although a significant portion comes from mucin that is sloughed off from the intestinal wall and is metabolized by mucin oligosaccharide degrading (MOD) bacteria in the colon. Mucin is a complex glycopeptide, where the glycan portion is typically branched and usually consists of reducing sugars, fucose, sialic acid and amino sugars. It is important to recognize that the oligosaccharide side chains of mucin help protect the peptide core from proteolytic digestion. Sialic acid confers significant hydrolytic resistance and thus it is a preferred embodiment of this invention that sialic acid be a part of the dendrite composition. Alternatively, A, B, or H blood group antigens (FIG. 2), which are part of mucin, would also confer resistance to hydrolysis in the small intestines. Bifidobacterium, which are a major species in the healthy colon are reported to have unique capabilities to hydrolyze N-acetylhexosamines. Thus it is a further preferred embodiment of this invention that A, B or H blood group antigens make up a portion of or all of the dendrite composition.

A. Dendritic Polysaccharide Encapsulation Platform for Peptide Drug Delivery

The present invention provides a means for a pharmaceutical composition comprised of a dendritic glycopeptide (i.e. the scaffold and the dendrite) for delivery of a pharmaceutically active compound. The pharmaceutically active compound can be a peptide, oligonucleotide or an active agent covalently bound to a peptide.

Peptide-based scaffolds are amenable to the preparation of combinatorial libraries by both chemical and recombinant methods. These libraries can in turn be screened to identify candidates that bind the pharmaceutical target through non-covalent/ligand interactions. Thus, peptides provide a powerful means of generating scaffolds suitable for use with peptide and non-peptide therapeutics that are not compatible with an approach that involves chemical/covalent ligation of the therapeutic agent to the scaffold. Thus it is a preferred embodiment of the invention that the peptide serves as a scaffold for dendritic encapsulation through the covalent attachment of polysaccharides. The peptide scaffold also serves as a ligand for non-covalent binding of a therapeutic peptide or peptide-drug conjugate. The therapeutic peptide is non-covalently attached through a ligand-receptor interaction, ionic bonding, or hydrogen bond to the scaffold peptide. Another potential advantage of this approach is that "ligation" reactions can be carried out under mild aqueous conditions, thus preserving the fold and integrity of a peptide therapeutic.

In another embodiment, the recombinant organism can be genetically engineered to glycosylate the peptide scaffold specifically. This would preclude the need to covalently add the polysaccharide dendrite.

Further, the peptide scaffold may serve as a point of covalent attachment for the therapeutic peptide or peptide-drug conjugate. The pharmaceutical composition of the present invention allows for the therapeutic peptide to be covalently attached to the dendritic glycopeptide. In this case the therapeutic peptide is covalently attached via an azide, amide, thioester, disulfide, ester, carbonate, carbamate or ureide bond to the side chains and/or the amino terminal and/or carboxy terminal residues of the scaffold.

In a further embodiment of the invention, the peptide therapeutic agent or therapeutic agent/peptide conjugate is attached to the peptide scaffold via a linker. In this case the linker is covalently attached via an azide, amide, thioester, disulfide, ester, carbonate, carbamate or ureide bond to the side chains and/or the amino terminal and/or carboxy terminal residues of the scaffold. The linker, then, is exposed to cleavage by intestinal enzymes after the polysaccharide dendrite is cleaved off the scaffold by bacterial glycosidases.

The present invention also embodies a pharmaceutical composition wherein a peptide containing a pharmaceutically active compound covalently attached to it is also attached to a dendritic glycopeptide. For example, a peptide-drug conjugate delivered through the present dendritic encapsulation composition.

B. Dendritic Polysaccharide Encapsulation Platform for Small Molecule Drug Delivery Another embodiment of the present invention includes a pharmaceutical composition wherein a pharmaceutically active small molecule is delivered to the colon. One advantage of the present invention is the specific delivery to the colon of pharmaceutically active compounds through protection of the active agent from enzymatic digestion by stomach and enzymes in the small intestine. This allows for improved delivery of the active agents to the colon.

It is an embodiment of the invention that the pharmaceutically active agent be dendritically encapsulated with a polysaccharide covalently attached to a scaffold. A further embodiment of the invention is that the scaffold is a peptide or oligonucleotide.

In yet a further embodiment of the invention the scaffold is a flavanol, diterpenoid or anthraquinone. Flavanols (e.g. quercitin), diterpenoids (e.g. stevioside), or anthraquinones (e.g., franguloside) are the aglycone portion of plants glycosides. Some of these plant glycosides are not absorbed in the small intestine and thus make it to the colon. Colonic microflora secrete β-glycosidases that can metabolize plant glycosides releasing the aglycone from the sugar moiety.

Figure 3:
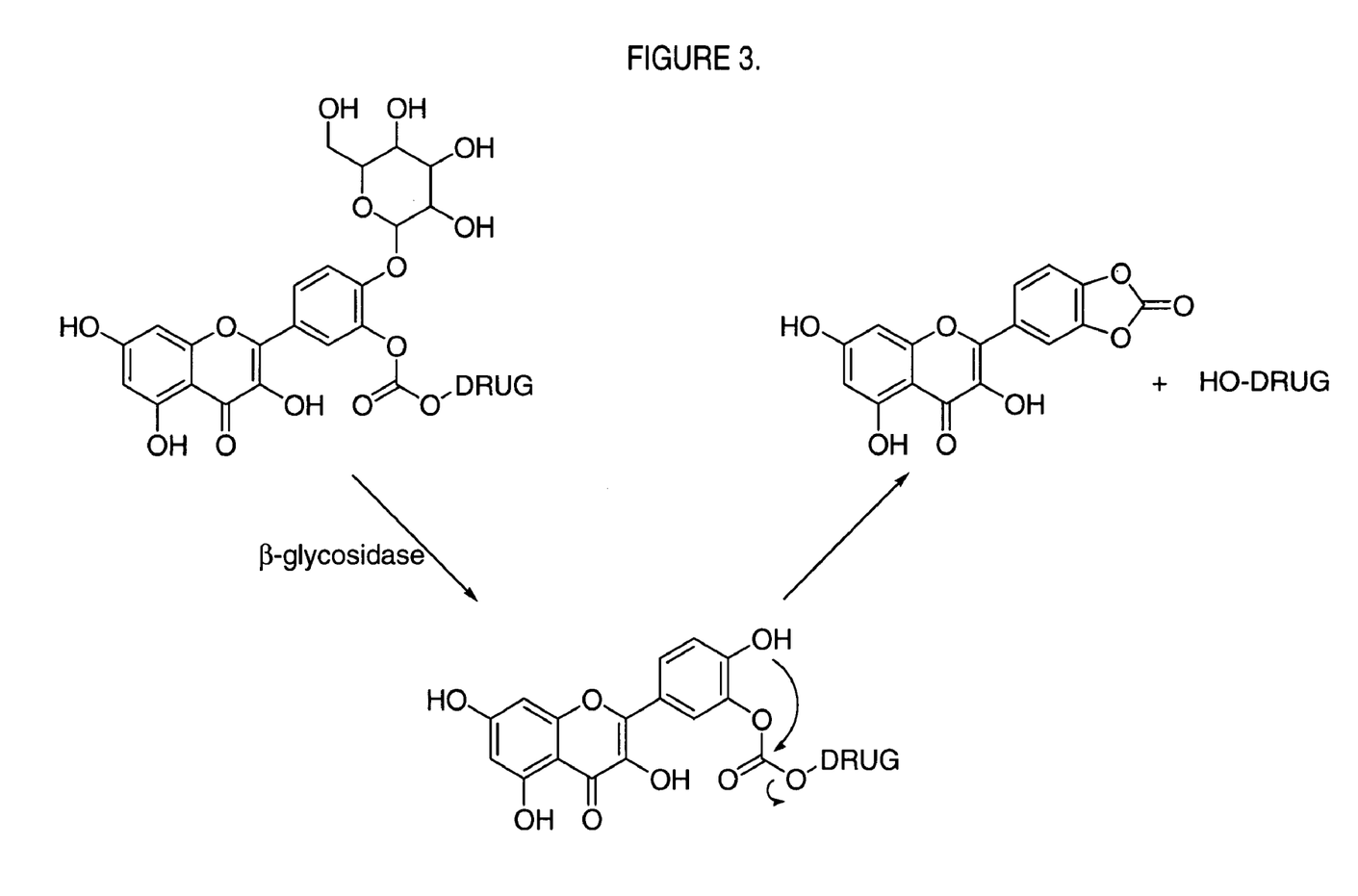
FIG. 3 depicts a schematic of Quercitin glycoside covalently attached to a drug via a carbonate linkage.

In an embodiment of this invention, an aglycone component of a glycoside can either be covalently attached to the active agent or ligated to the active agent through non-covalent bonding. In the case where the aglycone is covalently attached to the active agent, bacterial glycosidase action will release the aglycone, thus freeing up a hydroxyl group that, in turn, participates in an intramolecular rearrangement releasing the active agent intact. Thus it is a further embodiment of this invention that active agents can be released from a protective agent by an internal release mechanism (IRM) that is available only after enzymatic action occurs on the entire pharmaceutical construct (FIG. 3). In the case where the aglycone is not covalently attached the peptidase action will release the active agent by dissociation and no internal release mechanism is required for active agent release.

Figure 4:
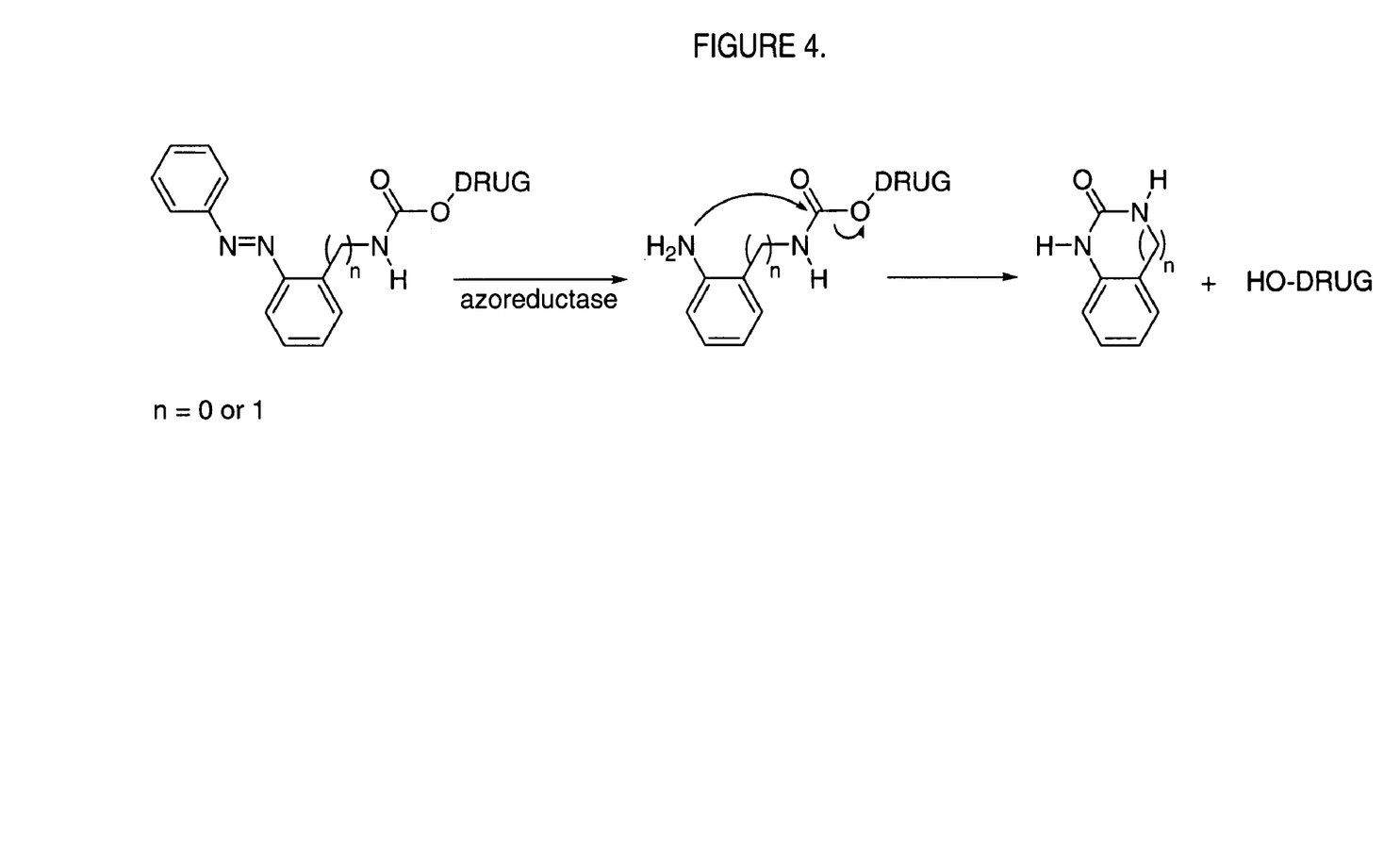
FIG. 4 depicts the schematic release of drug conjugated to an azo compound via carbonate linkage.
Figure 5:
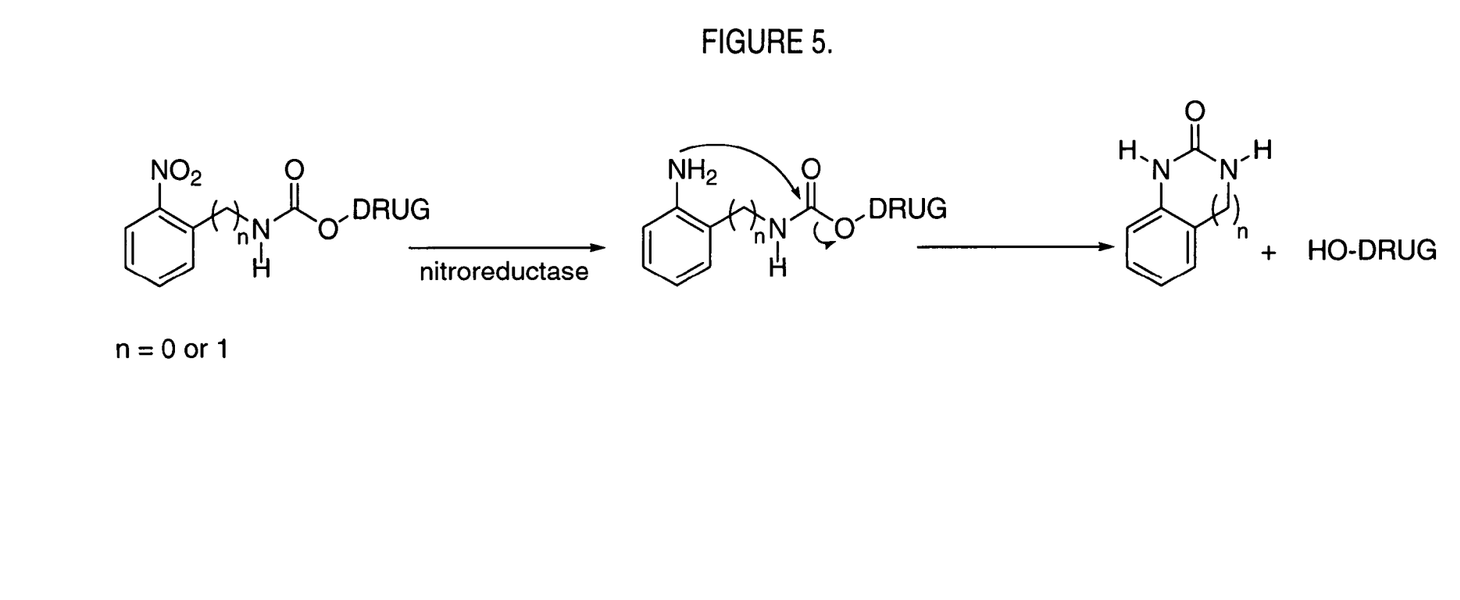
FIG. 5 depicts the schematic release of drug conjugated to a nitro compound via a carbonate linkage.

In another embodiment of the invention the scaffold is an azo compound or a nitro compound. Colonic bacteria possess the unique capability of reducing azo groups and nitro groups to amines. An active agent can be covalently attached to a molecule that also has an azo group (FIG. 4) or a nitro group (FIG. 5) in close proximity to the active agent bond. The polysaccharide dendrite is not shown in the figures but can be attached anywhere on the scaffolds. Further, if the azo scaffold or nitro scaffold can pass through the small intestines without being absorbed a polysaccharide dendrite would not be necessary.

An appropriately designed active agent conjugate will pass through the small intestines to the colon. In the colon, azoreductase or nitroreductase action will reduce the functionality to an amino group, which is now available for intramolecular cleavage of the bond that holds the active agent. Thus, it is a further embodiment of this invention to apply the IRM to masked amino groups as well. It is a preferred embodiment that the masked amino group be an azo compound or a nitro compound.

C. Dendritic Polysaccharide Encapsulation Platform for Drug Delivery Other than Colonic Another embodiment and advantage of the present invention is a pharmaceutical composition wherein a pharmaceutically active compound may be delivered parenterally. The present composition provides protection of pharmaceutically active compounds for example from serum enzymes, liver metabolism, and elimination by kidneys.

Another advantage and embodiment of the present invention allow for a pharmaceutical composition wherein a pharmaceutically active compound is delivered by inhalation. The present composition provides protection of pharmaceutically active compound from enzymes in the respiratory tract for example, elastase.

Other embodiments and advantages will be apparent from the non-limiting examples described below.

EXAMPLES

Hydrocodone, an opioid antagonist, was chosen as a model compound for the hypothesis that conjugates of opioid drugs can afford extended release.

Example 1

Preparation of the Chloroformate of 2,3-O-isopropylidene-1-methoxy-D-ribofuranose

Chloroformate of 2,3-O-isopropylidene-1-methoxy-D-ribofuranose

| Reagents | MW | Weight | mmoles | Molar Equivalents |
|---|---|---|---|---|
| 2,3-O-isopropylidene-1-methoxy-D-ribofuranose | 204 | 1.00 g | 3.85 | 1 |
| 20% Phosgene in toluene | — | 25 ml | — | — |

To a stirring solution of 20% phosgene in toluene under an inert atmosphere was added 2,3-O-isopropylidene-1-methoxy-D-ribofuranose via syringe. The resulting clear, colorless solution was stirred at ambient temperature for 30 minutes. After stirring, Ar(g) was bubbled through the solution for approximately 20 minutes to remove any excess phosgene. Solvent was then removed and product dried under vacuum for 18 hours. Product was used without further purification or characterization.

Example 2

Preparation of Ribo-Hydrocodone

| Reagents | MW | Weight | mmoles | Molar Equivalents |
|---|---|---|---|---|
| 1. Hydrocodone | 299 | 0.733 g | 2.45 | 1.0 |
| 1. LiN(TMS)$_2$ in THF | 1M | 3.68 ml | 3.68 | 1.5 |
| 1. DMF | — | 8 ml | — | — |
| 2. Ribose Chloroformate | — | — | 4.90 | 2.0 |
| 2. DMF | — | 3 ml | — | — |
| 3. 1M HCl | 1M | 10 ml | — | — |

To a solution of hydrocodone in DMF was added LiN(TMS)$_2$ in THF via syringe. The solution was stirred at ambient temperatures for 5 minutes then the chloroformate of ribose in DMF was added via syringe. The resulting solution was stirred at ambient temperatures for 2 hours. A TLC was taken (9:1 CHCl$_3$:MeOH; UV and 5% H$_2$SO$_4$ in MeOH; R$_{f(product)}$=~0.5). Reaction was neutralized to pH 7 with 1 M HCl. Solvent was removed. Crude product was taken up in CHCl$_3$ (50 ml), washed with water (3×50 ml), dried over MgSO$_4$, filtered and solvent removed. Final product was purified using preparative HPLC (10 mM CH$_3$COONH$_4$/MeCN; 0-20 min: 80/20 →0/100). Solid was collected as a clear, colorless glass (0.095g, 7% yield): $^1$H NMR (DMSO-d$_6$) δ 1.26 (s, 3H), 1.39 (s, 3H), 1.50 (m, 2H), 1.89 (s, 4H), 2.08 (m, 2H), 2.29(s, 4H), 2.40 (m, 2H), 2.88 (d, 1H), 3.08 (m, 1H), 3.25 (s, 3H), 3.73 (s, 3H), 4.12 (m, 2H), 4.28 (t, 1H), 4.58 (d, 1H), 4.72 (d, 1H), 4.97 (s, 1H), 4.98 (s, 1H), 5.70 (s, 1H), 6.66 (d, 1H), 6.75 (d, 1H). MS Calculated mass=529.2 Found=530.4 (M+H).

To the protected ribose intermediate was added 10 ml of 1 M HCl. The resulting solution was stirred at ambient temperatures for 2 hours. Solvent was removed and final product dried under vacuum. Solid was collected as a waxy, slightly yellow solid (0.092 g, quant.): $^1$H NMR (DMSO-$d_6$) δ 1.51 (t, 1H), 1.83 (d, 1H), 2.41 (dt, 1H), 2.27 (t, 1H), 2.63 (dd, 1H), 2.80 (s, 3H), 2.96 (m, 2H), 3.20 (m, 1H), 3.75 (s, 3H), 3.82-4.34 (br m, 12H), 5.15 (s, 1H), 5.72 (s, 1H), 6.75 (d, 1H), 6.88 (d, 1H), 11.37 (br s, 1H).

Preparation of the Chloroformate of 1,2:3,4-di-O-isopropylidene-D-galactopyranose

| Reagents | MW | Weight | mmoles | Molar Equivalents |
|---|---|---|---|---|
| 1,2:3,4-di-O-isopropylidene-D-galactopyranose | 260 | 1.00 g | 3.85 | 1 |
| 20% Phosgene in toluene | — | 20 ml | — | — |

Chloroformate of 1,2:3,4-di-O-isopropylidene-D-galactopyranose

To a stirring solution of 20% phosgene in toluene under an inert atmosphere was added 1,2:3,4-di-O-isopropylidene-D-galactopyranose via syringe. The resulting clear, colorless solution was stirred at ambient temperature for 30 minutes. After stirring, Ar(g) was bubbled through the solution for approximately 20 minutes to remove any excess phosgene. Solvent was then removed and product dried under vacuum for 18 hours. Product was used without further purification or characterization.

Preparation of Galacto-Hydrocodone

| Reagents | MW | Weight | mmoles | Molar Equivalents |
|---|---|---|---|---|
| 1. Hydrocodone | 299 | 0.223 g | 0.75 | 1.0 |
| 1. LiN(TMS)$_2$ in THF | 1M | 1.13 ml | 1.13 | 1.5 |
| 1. DMF | — | 5 ml | — | — |
| 2. Galactose Chloroformate | — | — | 1.49 | 2.0 |
| 2. DMF | — | 3 ml | — | — |
| 3. 1M HCl | 1M | 30 ml | — | — |
| 3. Acetone | — | 20 ml | — | — |

Galacto-Hydrocodone

To a solution of hydrocodone in DMF was added LiN(TMS)$_2$ in THF via syringe. The solution was stirred at ambient temperatures for 5 minutes then the chloroformate of galactose in DMF was added via syringe. The resulting solution was stirred at ambient temperatures for 2 hours. A TLC was taken (9:1 CHCl$_3$:MeOH; UV and 5% H$_2$SO$_4$ in MeOH; R$_{f(product)}$=~0.5). Reaction was neutralized to pH 7 with 6 M HCl. Solvent was removed. Final product was purified using preparative TLC (0-10% MeOH in CHCl$_3$). Solid was collected as a white powder (0.180 g, 41% yield): $^1$H NMR (DMSO-$d_6$) δ 1.28 (2s, 6H), 1.37 (s, 3H), 1.44 (3, 3H), 1.49 (m, 2H), 1.88 (dt, 1H), 2.08 (m, 2H), 2.29 (s, 4H), 2.40 (m, 2H), 2.90 (d, 1H), 3.09 (s, 1H), 3.73 (s, 3H), 3.99 (dd, 1H), 4.14 (t, 1H), 4.26 (dt, 2H), 4.39 (d, 1H), 4.63 (d, 1H), 4.95 (s, 1H), 5.48 (d, 1H), 5.68 (d, 1H), 6.65 (d, 1H), 6.74 (d, 1H); MS Calculated mass=585.6 Found=586.4 (M+H).

To the protected galactose intermediate was added 30 ml of 1 M HCl and 20 ml acetone. The resulting solution was stirred at ambient temperatures for 3 hours. Solvent was removed and final product dried under vacuum. Solid was collected as a white solid: MS Calculated mass=505.5 Found=506.4 (M+H).

General Scheme for the Preparation of Disaccharide-Hydrocodone Conjugates

The protected mannofuranose (1) has been converted to the trichloroacetimidate (2) as described below. Based on literature precedent, this can in turn be coupled to an orthogonally protected xylose (3), which affords the corresponding disaccharide (4). Disaccharide formation is promoted by the addition of a catalytic amount of acid. Use of an orthogonal protection scheme allows the selective removal of the silyl protecting group using tetrabutyl ammonium fluoride in the presence of the isopropylidene groups, affording the free primary alcohol (5). Employing methods already described in the preparation of galactose and ribose conjugates, this alcohol can then be converted to the ch0loroformate (6) and in turn coupled to the hydrocodone-enolate (7), resulting in the carbonate (8). Deprotection of (8) using standard protocols affords the hydrocodone-disaccharide conjugate (9)

Preparation of the trichloroacetimidate of mannofuranose (2)

Dissolved 2,3:5,6-Di-O-isopropylidene-D-mannofuranose (1, 0.50 g, 1.9 mmol) in 5 ml of anhydrous dichloromethane. Then, trichloroacetonitrile (0.67 ml, 6.7 mmol) was added to the solution followed by dry $K_2CO_3$ (0.54 g, 0 3.8 mmol). The reaction was then allowed to stir over night at room temperature under argon. Qualitative thin-layer chromatography (2:1 hexanes/acetone) of the reaction mixture indicated that the desired trichloroacetimidate had been formed, based on the disappearance of the spot corresponding to the mannofuranose starting material that correlated with the appearance of a new faster-running spot. This is consistent with literature precedence. The reaction was then filtered through fritted glass and the filtrate collected and freed of solvent by rotary-evaporation under high vacuum. This resulted in a viscous oil that solidified with storage over night under high vacuum.

The invention claimed is:

1. A composition comprising hydrocodone covalently attached to a sugar.
2. The composition of claim 1 wherein said sugar is ribose.
3. The composition of claim 1 wherein said sugar is galactose.
4. The composition of claim 1 wherein said sugar is a disaccharide.
5. The composition of claim 1 wherein said sugar is a mannofuranose.

* * * * *